United States Patent [19]
Gönner

[11] 3,973,792
[45] Aug. 10, 1976

[54] CONNECTING DEVICE FOR CONNECTING CHROMATOGRAPHIC SEPARATING COLUMNS OF GLASS

[75] Inventor: Winfried Karl Gönner, Uberlingen, Germany

[73] Assignee: Bodenseewerk Perkin-Elmer & Co. GmbH, Uberlingen, Germany

[22] Filed: Nov. 3, 1975

[21] Appl. No.: 627,850

Related U.S. Application Data

[62] Division of Ser. No. 432,805, Jan. 14, 1974.

[52] U.S. Cl. .............................. 285/341; 285/356
[51] Int. Cl.² .................. F16L 17/00; F16L 19/06; F16L 19/08; F16L 21/02
[58] Field of Search .......... 285/341, 342, 343, 238, 285/351, 356, 357, DIG.12

[56] References Cited
UNITED STATES PATENTS

| 2,190,419 | 2/1940 | Evarts | 285/356 X |
| 2,308,757 | 1/1943 | Hulsberg | 285/356 X |
| 3,362,731 | 1/1968 | Gasche et al. | 403/333 X |
| 3,756,632 | 9/1973 | Riggs et al. | 285/356 X |

FOREIGN PATENTS OR APPLICATIONS

| 1,027,172 | 5/1953 | France | 285/341 |
| 1,154,990 | 4/1958 | France | 285/341 |
| 1,423,894 | 11/1965 | France | 285/341 |
| 1,207,736 | 12/1965 | Germany | 285/341 |

Primary Examiner—Wayne L. Shedd
Attorney, Agent, or Firm—S. A. Giarratana; F. L. Masselle; J. M. O'Meara

[57] ABSTRACT

In a connecting device for connecting chromatographic separating columns of glass to terminal fittings on a chromatographic apparatus, each end of the column is surrounded by a metallic sleeve. A sleeve made of synthetic plastic material, which is of substantially stable shape at least up to a temperature of 350° centigrade even if subjected to pressure, is interposed between said end and said metallic sleeve. A preferred material is polyimide. The plastic sleeve has at least one conical end face and is held in sealing engagement with the end of the separating column, on one hand, and with the metallic sleeve, on the other hand, by a sleeve shaped thrust member, which is axially movable relative to the metallic sleeve to exert an axial force on said plastic sleeve. A radial sealing force is exerted on the snthetic plastic sleeve through its conical end face by an abutting complementary conical surface. Conventional connecting means for gas-tightly and detachably connecting the ends of the column to the terminal fittings of the apparatus are provided on the metallic sleeve. In another embodiment the plastic sleeve is made of polytetrafluoroethylene, and the sleeve is held in sealing engagement with the metallic sleeve and the end of the separating column at an adjustable minimum axial pressure. This pressure is exerted through a sleeve-shaped thrust member by a compressed spring.

5 Claims, 2 Drawing Figures

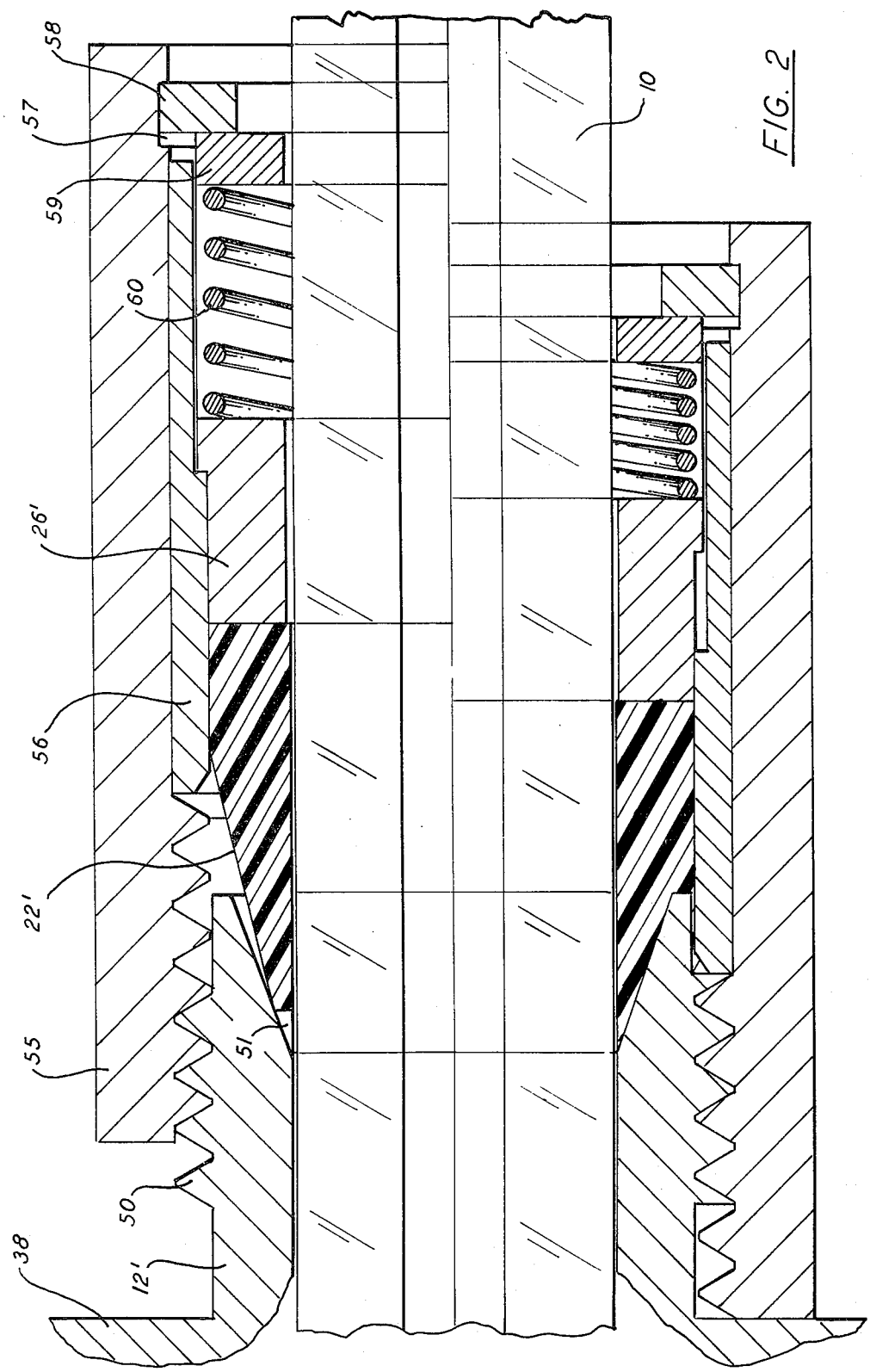

CONNECTING DEVICE FOR CONNECTING CHROMATOGRAPHIC SEPARATING COLUMNS OF GLASS

This is a division of application Ser. No. 432,805, filed Jan. 14, 1974.

BACKGROUND AND SUMMARY OF THE INVENTION

This invention relates to a connecting device for connecting chromatographic separating columns of glass to terminal fittings on a chromatographic apparatus.

The published German Pat. No. 2,029,738 shows a connection fitting for a laboratory apparatus of glass having a connection socket which is provided with grooves to retain a hose pushed thereon. A threaded bushing is slid on the connection socket and a sealing ring of rubber-like resilient material, such as a piece of rubber hose, is pushed on the connection socket, the sealing being deformed thereby to closely engage the connection socket and to fill also the grooves therein. The connection fitting slid thereon is threaded with an internal thread on the external thread of the threaded bushing, and the sealing ring is deformed between the connection fitting and the threaded bushing by tightening the thread and is tensioned against the connection socket. The bore of the connection fitting has an inclined shoulder, and, correspondingly, the bore of the threaded bushing has a flaring inclined shoulder at its end facing the sealing ring. A connection fitting of the type having a sealing ring of rubber-like material is neither intended nor suitable for use at high temperatures, such as 350° centigrade, occurring in gas-chromatographic separating columns, as the material of the sealing ring is not able to withstand these temperatures.

Swiss Pat. No. 509,591 shows a closure device for a chromatographic tube in which two sealing rings of rubber-like material are interposed between a plug or care member and the internal wall of the chromatographic tube and a spacer tube is arranged between these sealing rings. The sealing rings have trapeziodal cross sections flaring outwardly, whereby they can be pressed by axial pressure against the internal wall of the tube. This axial pressure is exerted by the annular part of a thrust member the conical end face of which engages a conical end face of one sealing ring. A conical surface of a flange provided on the plug engages a conical end face of the other sealing ring. The thrust member is axially adjustable relative to the core member. Also this closure device is neither intended nor suitable for use at high temperatures because of the material of the sealing ring.

There are various other connecting devices for gas-tightly and sealingly connecting the ends of separating columns to terminal fittings on the apparatus. These are the conventional means for detachably and sealingly connecting of tubes, such means comprising conical sealing end faces which are tightened by means of a screw cap. Using such connecting devices with chromatographic columns made of glass encounters problems in practice. The presently available detachable connecting devices for chromatographic separating columns made of glass are adapted for use at temperatures up to 230° centigrade. They may be used for a short time and without quick temperature variations up to temperatures of 300° centigrade. In recent time, however, gas-chromatography requires glass column connections which remain gas-tight also, if a temperature program up to about 350° centigrade is used, and which are still easily detachable. It is to be noted that gas-chromatography requires frequent interchanging of the separating columns and thus a correspondingly frequent detaching of the connections. The prior art glass column connections are not adapted to meet these requirements.

It is an object of the invention to provide a connecting device for connecting chromatographic columns of glass to the terminal fittings on the apparatus, said connecting device being easily detachable, gas-tight up to 350° centigrade and indifferent to thermal shocks.

According to the invention, there is a connecting device for connecting chromatographic separating columns of glass comprising connecting means for gas-tightly and detachably connecting the ends of the separating column to terminal fittings on a chromatographic apparatus. The ends of the column of glass are surrounded by a metallic sleeve, a sleeve of synthetic plastic having at least one conical end face being interposed therebetween. The synthetic plastic sleeve is held in sealing engagement with the separating column, on one hand, and with the metal sleeve, on the other hand, by a sleeve shaped thrust member, which is axially adjustable relative to the metallic sleeve. A radial sealing force is exerted on the synthetic plastic sleeve through its conical end face by an abutting complementary conical surface. The connecting means are provided on the metal sleeve.

According to one aspect of the invention the synthetic plastic sleeve consists of a synthetic plastic material which is of substantially stable shape at least up to a temperature of 350° centigrade even if subjected to pressure.

The invention is based on the discovery that a sufficient radial sealing force can be achieved by the wedge effect through the conical end faces even with a synthetic plastic material which has no rubber-like characteristics but is of substantially stable shape. Thus a temperature resistant synthetic plastic material such as polymide can be used, and, thereby, such a connecting device is adapted to be used for connecting chromatographic separating columns which are subjected to a temperature program up to 350° centigrade.

There are materials which, though they are of substantially stable shape and have no rubber-like characteristics, tend to flow under the influence of the pressure and of the high temperature or are subject to material losses due to evaporation, whereby the axial pressure exerted by the thrust member and causing the sealing force relaxes and the seal becomes leaky. A material of this type is, for example, polytetrafluoroethylene. Due to its other especially advantageous characteristics this type of material cannot always be replaced by other materials.

It is a further object of the invention, to provide a connecting device of the type mentioned hereinbefore in which the sealing synthetic plastic sleeve may be made of a material having a tendency to flow or vaporize under the influence of pressure and temperature, and which, nevertheless, remains gas-tight and permits repeated use of any particular sealing plastic sleeve.

It is a more specific object of the invention to provide a connecting device of the type described hereinbefore, in which the sealing synthetic plastic sleeve is made of polytetrafluoroethylene.

According to another aspect of the invention the plastic sleeve is held at an adjustable minimum axial pressure in sealing engagement with the metal sleeve and the separating column. For this purpose one end face of a sleeve-shaped thrust member engages the adjacent end face of the synthetic plastic sleeve, and a spring compressible by means of an axial adjusting device abuts the other end face of the thrust member.

DESCRIPTION OF THE DRAWINGS

FIG. 2 is a vertical sectional view similar to FIG. 1 of a second embodiment of a connecting device of the invention.

DESCRIPTION OF SPECIFIC EMBODIMENTS

Figure 1:
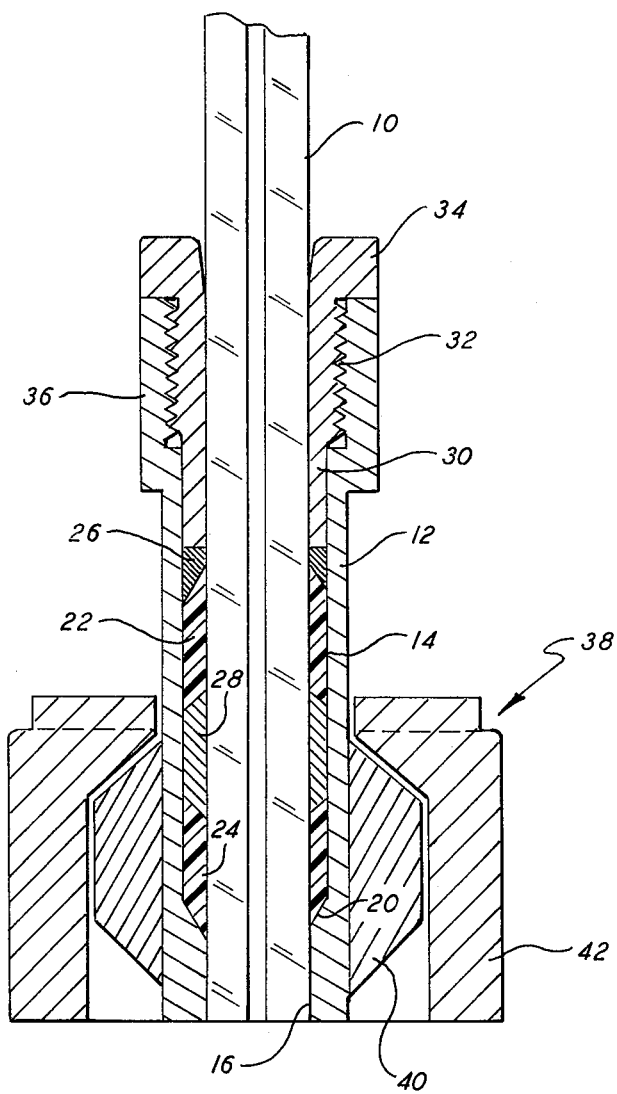
FIG. 1 is a vertical sectional view of a first embodiment of a connecting device of the invention as applied to one end of a chromatographic column made of glass.

Referring to FIG. 1, reference numeral 10 designates a gas-chromatographic separating column made of glass which has its end projecting into a metallic sleeve 12 which surrounds the separating column 10 at a distance. The metallic sleeve 12 has a reduced internal diameter at its end adjacent the apparatus said reduced internal diameter being slightly less than the external diameter of the separating column 10. A conical shoulder 20 is formed between the section 14 of the greater internal diameter and the section 16 of the reduced internal diameter.

Two synthetic plastic sleeves 22 and 24 are interposed as well as two sleeve-shaped thrust members 26 and 28 between the separating column 10 and the metallic sleeve 12 in the section 14. The plastic sleeves 22 and 24 have a convexly conical front face and a concavely conical front face each. The convexly conical front face of the plastic sleeve 24 abuts the conical shoulder 20. The thrust member 18 has two convexly conical front faces of which one abuts the concavely conical front face of the plastic sleeve 24. The other convexly conical front face abuts the concavely conical front face of the plastic sleeve 22, whereas the thrust member 26 has a concavely conical front face abutting the convexly conical front face of the plastic sleeve 22. With an axial pressure exerted on the thrust member 26, the thrust member 28 and the plastic sleeves 22 and 24, by a wedging action, the plastic sleeve 22 will be pressed at its upper end inwardly against the outer surface of the separating column 10 and at its lower end inwardly against the inner surface of section 14 of sleeve 12. Similarly, the plastic sleeve 24 will be pressed at its upper end outwardly against the inner surface of section 14 of metallic sleeve 12 and at its lower end against the outer surface of the separating column 10. As already mentioned, the plastic sleeves may consist of polyimide.

A polyimide which has proved useful for the purposes of this invention is a polyimide having graphite added commercially available from Du Pont de Nemours, Wilmington (Delaware) under the trade mark Mespel SP 21.

The axial pressure is exerted on thrust member 26 by a thrust sleeve 30 which has its external threads screwed into internal threads 32 of the metallic sleeve 12. The thrust sleeve 30 projects beyond the end of the metallic sleeve 12 and has an annular hexagonal head 34 at its projecting end. Also the metallic sleeve 12 has an annular hexagonal head 36 at its end.

Conventional connecting means 38 for gas-tight and detachable connection of tubes are provided at the lower end of the metallic sleeve 12. These connecting means may, for instance, comprise a sealing body 40 and a retaining nut 42. By these connecting means the separating column can be connected to the terminal fittings of the apparatus without the glass or the sealing means (plastic sleeves 22 or 24) in contact with the glass being subjected to any changing loads.

The torque between the metallic sleeve 12 and the thrust sleeve 30 required to exert the axial thrust on the thrust sleeve should be approximately in the order of magnitude of 10 kp-centimeter. The metal parts may consist of stainless steel.

The connecting device according to this invention can be used in gas-chromatographic apparatus up to an operating temperature of at least 662°F also when using a temperature program. The detachable connection is made by using the connecting means common in gas-chromatographic apparatus, so that insofar no changes in the apparatus are required.

The connecting device according to this invention could possibly also be used for connection of other glass parts, for instance, to connect nozzles consisting of glass or the like for flame ionization detectors.

Another embodiment of this invention is shown in FIG. 2 of the drawings and will now be explained and described.

The righthand portion of FIG. 2 illustrates the connecting device in the open, i.e. unloaded position and the lefthand portion shows the device in the closed, i.e. loaded position.

In FIG. 2 reference numeral 12' designates a metallic sleeve, the separating column 10 made of glass extending therethrough, sleeve 12' is provided at its one end with connecting means generally referenced 38 to which the metallic sleeve 12' is secured. Sleeve 12' is provided with an externally threaded portion 50 close to its end remote from the apparatus. Internally, this end of the metallic sleeve 12' has a conical recess 51. A cap body 55 having internal threads is guided on the externally threaded portion 50. The internal threads extend part of the length of the internal walls of the cap body 55. Directly adjacent the internal threads is an intermediate sleeve 56 which has a tapering end extending close to a groove 57. Groove 57 is disposed near the other end of the cap body 55. A retaining ring 58 is inserted into the groove 57 with a slip ring 59 partly abutting the inner surface of this retaining ring. The slip ring 59 has a smaller inner diameter and a smaller outer diameter than the retaining ring 58, however, its inner diameter is wider than the outer diameter of the separating column 10. The retaining ring 58 and the slip ring 59 together form an abutment for a spring 60 arranged between the intermediate sleeve 56 and the separating column 10 and which has its other end abutting a front face of the thrust member 26'. The spring abutment of the thrust member 26' has a larger diameter than the remaining portion of this thrust member. The thrust member directly abuts the intermediate sleeve 56, however, has an inner diameter larger than the outer diameter of the separating column 10. The thrust member 26' has a plane front face at the end remote from the spring abutment, against which a plastic sleeve 22' is directly supported. The outer diameter of plastic sleeve 12' is also large enough that it abuts the intermediate sleeve 56 with an outer surface thereof. The inner diameter of the plastic sleeve 22' is slightly larger than the outer diameter of the separating column 10. At its end on the side of the apparatus the plastic sleeve 22' is provided with a conical front face corresponding to the recess 51 on the metallic sleeve 12'.

The cap body 55 can, for example, be hexagonal on its outside. Upon rotation of the cap body on the externally threaded portion 50 of the metallic sleeve 12' in a direction towards the connecting means 38, the intermediate sleeve 56 and at the same time also the abutment for the spring 60, namely the slip ring 59 and the retaining ring 58 move in the same direction. Thereby, initially the cone-shaped front face of the plastic sleeve 22' is inserted into the cone-shaped recess 51 on the metallic sleeve 12' and upon further rotation of the cap body 55 is finally pressed into this recess under the pressure of the compressed spring 60. The intermediate sleeve 56 is slidable on the plastic sleeve 22' and on the thrust member 26' so that a sealing enclosure of the plastic sleeve 22' is achieved. The spring 60 may be compressed to an extent that even at an elevated temperature at which the material of the plastic sleeve starts flowing or evaporates to small proportions, a sealing abutment of the plastic sleeve both against the recess 51 in the metallic sleeve 12', against the intermediate sleeve 56, and against the separating column 10 is maintained, since under the influence of the spring 60 the contact pressure is maintained to the extent required for the sealing.

The connecting device hereinbefore described ensures that under the test conditions always the minimum pressure required for sealing is applied to the plastic seal 22'. It further enables an application of the connecting device also in connection with temperature-programmed gas chromatographs wherein a frequent and possibly rapid temperature change between ambient temperature and temperatures of above 482°F occurs. The connecting device is repeatedly applicable, and after a temperature change no exchange of a "used-up" plastic sleeve 22' against a new plastic sleeve is required.

I claim:

1. A connecting device for coupling glass chromatographic separating columns to chromatographic instruments comprising:
   a. a metallic sleeve surrounding an end of such a column;
   b. a sleeve of synthetic plastic material, possessing dimensional stability at temperatures of up to at least 350°C, coaxially surrounding said column adjacent said metallic sleeve, said plastic and metallic sleeves having generally complementary conical end surfaces in confronting relation and partially overlapping;
   c. a sleeve-shaped thrust member coaxially disposed about said column adjacent said plastic sleeve and axially displaceable relative to said metallic sleeve;
   d. an axial adjustment sleeve coaxially surrounding said thrust member and in threaded engagement at one end with said metallic sleeve; and
   e. resilient force-exerting means between said thrust member and the other end of said adjustment sleeve to exert an axial force on said plastic sleeve to generate a radial sealing force between the plastic sleeve, the column, and the metallic sleeve by abutting coaction of said complementary end surfaces.

2. A connection device according to claim 1 further comprising an intermediate sleeve member interposed radially between said thrust member and adjustment sleeve and having one end, proximate said column end, in sliding contact with said plastic sleeve and its opposite end extending beyond said thrust member.

3. A connecting device according to claim 2 wherein said forceexerting means include:
   a. means defining an internal spring abutment adjacent said opposite end of said adjustment sleeve; and
   b. compressible spring means coaxially disposed within said opposite end of the adjustment sleeve between said spring abutment and said thrust member.

4. A connecting device according to claim 3 wherein said spring abutment comprises:
   a. an annular groove in the internal surface of said adjustment sleeve adjacent said opposite end thereof;
   b. a retainer ring removably engaged in said groove; and
   c. a slip ring coaxially disposed with respect to said retainer ring between said spring and retainer ring.

5. A device according to claim 4 wherein said slip ring has an outer diameter larger than the inner diameter of the retainer ring but smaller than the outer diameter of the retainer ring and said slip ring has a smaller inner diameter than the retainer ring.

* * * * *